(12) United States Patent
Lomask et al.

(10) Patent No.: US 8,316,849 B2
(45) Date of Patent: Nov. 27, 2012

(54) INTEGRATED VENTILATOR WITH CALIBRATION

(75) Inventors: Joseph Lomask, Wilmington, NC (US); Richard A. Larson, Winchester (GB)

(73) Assignee: Buxco Electronics, Inc., Sharon, CT (US)

( * ) Notice: Subject to any disclaimer, the term of this patent is extended or adjusted under 35 U.S.C. 154(b) by 1261 days.

(21) Appl. No.: 12/103,074

(22) Filed: Apr. 15, 2008

(65) Prior Publication Data

US 2008/0264419 A1 Oct. 30, 2008

Related U.S. Application Data

(60) Provisional application No. 60/926,369, filed on Apr. 26, 2007.

(51) Int. Cl.
*A62B 7/00* (2006.01)
*A62B 18/02* (2006.01)
*F16K 31/02* (2006.01)

(52) U.S. Cl. ......... 128/204.23; 128/200.24; 128/204.18; 128/205.25

(58) Field of Classification Search ............. 128/200.24, 128/203.12, 203.13, 203.14, 203.15, 204.18, 128/204.21, 204.22, 204.23; 600/532, 529
See application file for complete search history.

(56) References Cited

U.S. PATENT DOCUMENTS

| | | | |
|---|---|---|---|
| 3,923,056 A * | 12/1975 | Bingmann et al. | ....... 128/204.21 |
| 4,393,869 A | 7/1983 | Boyarsky et al. | |
| 4,481,944 A | 11/1984 | Bunnell | |
| 4,527,557 A * | 7/1985 | DeVries et al. | .......... 128/204.23 |
| 4,838,257 A | 6/1989 | Hatch | |
| 5,072,737 A | 12/1991 | Goulding | |
| 5,092,326 A | 3/1992 | Winn et al. | |
| 5,183,038 A | 2/1993 | Hoffman et al. | |
| 5,303,698 A | 4/1994 | Tobia et al. | |
| 5,355,893 A * | 10/1994 | Mick et al. | ..................... 600/532 |
| 5,692,497 A | 12/1997 | Schnitzer et al. | |
| 5,752,506 A | 5/1998 | Richardson | |
| 6,196,222 B1 | 3/2001 | Heinonen et al. | |
| 6,390,091 B1 | 5/2002 | Banner et al. | |
| 6,564,798 B1 | 5/2003 | Jalde | |
| 6,571,796 B2 | 6/2003 | Banner et al. | |
| 6,591,835 B1 | 7/2003 | Blanch | |
| 6,932,084 B2 | 8/2005 | Estes et al. | |
| 2004/0249300 A1* | 12/2004 | Miller | ........................... 600/532 |
| 2005/0109340 A1 | 5/2005 | Tehrani | |
| 2007/0016391 A1* | 1/2007 | Minoguchi et al. | ............. 703/11 |

* cited by examiner

*Primary Examiner* — Annette Dixon
(74) *Attorney, Agent, or Firm* — MacCord Mason PLLC

(57) ABSTRACT

An integrated respiratory ventilation system and method for its calibration is described. The system includes a ventilator having air conduits, transducers adapted to emit signals proportional to the level of air pressure or air flow within the air conduits, and inspiration, expiration and exhaust ports. A processor-controlled calibrator is in communication with one or more of the air conduits. A preferred calibrator includes a water-filled outer column and a vertically aligned inner column extending into the outer column, the inner column having an upper end in communication with at least one of the ports. A processor controls the opening and closing of the ports and the level of air pressure in, and air flow from, the inner column to measure the level of transducer signals at two known pressures and two known flows. The processor uses the measured transducer signals to calibrate the transducer.

20 Claims, 13 Drawing Sheets

Typical System Components

-- PRIOR ART --

INTEGRATED VENTILATOR WITH CALIBRATION

This application claims the benefit of the filing date of U.S. Provisional Application Ser. No. 60/926,369, filed Apr. 26, 2007.

BACKGROUND OF THE INVENTION (1) Field of the Invention

The present invention relates to a method and apparatus for automatically calibrating the pressure and flow within a ventilator, and in particular to a method and apparatus for automatically calibrating the flow, lung pressure, mouth pressure and reservoir pressure signal transducers within a ventilator responsive to calibration measurements.

(2) Description of the Prior Art

Researchers often evaluate the performance of the lung under various test conditions. One common way to evaluate the lung requires the subject to be anesthetized and ventilated with a respirator. In addition, compounds may be delivered through a special aerosol apparatus which is integrated with the ventilator. During the testing, the animal's airflow in and out of his lung is measured along with one of many possible lung pressures. Which lung pressure to measure is dependent upon the experimental needs of the researcher. Typically, this apparatus is connected to a host PC to perform the data collection.

A ventilator is generally comprised of a source of predetermined air pressure, an inspiration port connectable to the trachea of a test subject, a conduit from the air source to the inspiration port, and means to control the volume of air flowing through the conduit from the air source to the inspiration port. The ventilator also includes an expiration port in communication with the test subject to remove inspired air, and an exhaust port to discharge air or for collection of the expired air for analysis.

The inspiration and expiration ports are normally connected via a Y-tube to the subject's trachea. The exhaust port may be vented to the atmosphere or connected to means to capture expired gases or to maintain a minimum positive pressure on the lung, which is known as positive end-expiratory pressure, or PEEP. The ventilator also optionally includes a nebulizer inline between the ventilator inspiration port and the trachea.

Flow and pressure signals from the subject apparatus, e.g., an enclosure surrounding the subject, are conditioned by a preamplifier prior to reading and analysis of the results by a computer, normally the host PC. The ventilator, preamplifier and a nebulizer controller can be combined with a central processor into a control unit that is in communication with, and receives commands and parameters from the host computer.

Operation of the ventilator is controlled in accordance with a preset program by a processor, which determines the pressure of the air source, the volume of air flowing out of the inspiration port, and opening and closing of inspiration and expiration ports. Control of the air pressure and flow is normally achieved by opening and closing of valves within conduits in the ventilator, with the pressure and flow within the conduits at a given time being measured by inline transducers that transmit electrical signals proportional to pressure or flow to the processor.

In order for the ventilator to function properly, these pressure and flow signals must be precise. Therefore, before operation of the ventilator, it is the practice to calibrate each of the transducers to ensure that the electrical signals accurately reflect the measured pressure or flow. Historically, this calibration has been done manually by applying a predetermined pressure or flow within the relevant conduits and measuring the transducer voltages at given known pressures and flows. This procedure is time consuming and may be inaccurate due to human error.

Therefore, there is a need for a method and apparatus for automatically calibrating a ventilator, and specifically for a method and apparatus for calibrating the pressure and flow transducers signals in a ventilator.

SUMMARY OF THE INVENTION

Generally, these objectives are achieved by an apparatus comprised of a ventilator, a processor and a calibration means, or calibrator, attachable to the ventilator and operable by the processor to calibrate the ventilator transducer signals.

The ventilator of the invention is comprised of inspiration and expiration ports connectable to a test subject, a pressurized air source, a conduit, e.g., tubing, for connecting the air source to the inspiration port to enable the flow of pressurized air from the air source. The ventilator also includes an expiration port connectable to the test subject for removing expired air from the test subject, and an exhaust port for exhausting expired air. Means is also provided for measuring pressure and flow of expired air and for transmitting the pressure and flow information, normally via a preamplifier, to the processor.

The ventilator also includes various valves to control the flow of air through different parts of the ventilator and measurement means, normally transducers, for measuring pressure or flow within the different ventilator conduits. Means is also included for communication between the processor and the various ventilator valves and measurement means to enable the processor to control the flow of air through the ventilator.

The processor acts in accordance with a software program and user inserted parameters to control the flow of air through the ventilator conduits, including the length of time that the air is permitted to flow. During operation, the processor also receives signals from the various measurement means in the ventilator conduits proportional to the pressure or flow within the conduits. This information is used by the processor to quantitatively determine the pressure or flow based on the level of the signals received.

For example, if the measurement means are transducers, each transducer will transmit an electrical signal, e.g., a voltage signal, to the processor that is proportional to the pressure or flow in the conduit. The processor is then able to calculate the pressure or flow from this voltage signal from the relationship between the voltage signal and the pressure or flow.

The measurement means signal, e.g., the voltage signal from transducers, must accurately reflect the level of pressure or flow. That is, each measurement means, before use on the system for ventilation of a test subject, must be calibrated so that the signal level in fact accurately corresponds to the pressure or flow level.

Instead of calibrating the transducers manually, the present system also incorporates a means for automatically calibrating the transducers, thereby saving time and increasing accuracy. Basically, the present system includes a calibrator attachable to the inspiration and expiration ports of the ventilator to enable the processor to apply known pressures and flows to the system, and determine the signal level of each transducer upon application of the known pressure or flow.

From this signal and the signal level when there is no applied pressure or flow, a linear relationship between the signal level and pressure or flow can be calculated. Then, during use of the ventilator for ventilating a test subject, the processor can determine the precise level of pressure or flow using this relationship and compare the level to the desired level.

Generally, the calibrator is comprised of a water-filled outer column with a vertically aligned inner column, or rigid tube, extending into the outer column, a piece of tubing connecting the main test chamber to the exhaust port on the ventilator, and a plug which blocks the tracheal port of the Y connector. The inner column includes an upper end above the level of the water in the outer column, and a lower end in the water. The upper end is in communication with the inspiration port of the ventilator.

Using this calibration apparatus, two known pressure levels and two known flows can be measured, along with the signal levels of the transducers at these levels. Assuming a straight line relationship between the pressure levels and the signal levels, the pressure at any signal level can then be calculated.

A first pressure level is measured when nothing is flowing into the inner column and the water level in the inner column is the same as the water level in outer column, the apparatus is applying 0 cm $H_2O$ and zero flow. The signal levels of the transducers to be calibrated are read at this first pressure level.

To measure a second pressure level, the processor opens the inspiration port valve fully, while simultaneously closing the reservoir bleed port fully. The processor applies a known pressure level as provided by calibration apparatus by flowing air through the inspiration port and closing expiration port, and waiting until the air bubbles out the bottom of the inner column. At this time, the inspiration port is closed, trapping the air in the inner column, with no bubbles flowing, and the second pressure reading is taken. The signal levels of the transducers to be calibrated are also read at this second pressure level.

When the air flowing into the inner column is stopped and the air is allowed to flow out of the inner column, then a known amount of air will be forced by the water pressure out the top of the inner column. This known volume of air will be forced out within a limited and known amount of time. Since the volume of the inner column and the maximum time it takes to force the volume out are known, the average flow rate that the air moved during that time can be calculated. That average flow rate is the second known flow for calibration, the first flow being zero flow.

Lung pressure, mouth pressure, and reservoir pressure transducers are calibrated using the above procedure with the signals measured at the first and second pressure levels. Subject air flow is calibrated from the linear relationship between the above two known calibration flows and the signals taken at the subject air flow transducer at each flow. In calibrating subject air flow, the processor closes the expiration port and applies a known flow with the inflation port open until air bubbles exit the bottom of the inner column. The inspiration port is then closed and the expiration port is opened, which releases the air in the inner column and allows the air to be forced into the expiration port out of the exhaust port. Since the exhaust port is connected to the test chamber or the subject flow measurement apparatus, the flow from the inner column is in turn forced through the flow measurement apparatus. The average flow over a region of time can then be calculated based on the known volume of the inner column and the time that it takes to exhaust the air.

Calibration of inspiration flow is similar to calibration of subject air flow. This must be calibrated after the mouth pressure has been calibrated. The processor fills the inner column to some level. The processor can measure the level by measuring the pressure on the mouth pressure transducer. Knowing the pressure on the mouth pressure, we know the level inside the inner column. Since the inner column is uniformly bored, and the level inside the inner column is proportional to the volume of air in the inner column, the volume filled can be calculated directly by measuring the mouth pressure. The average flow is then known by dividing that known volume by the time it takes to fill that volume.

DETAILED DESCRIPTION OF THE INVENTION

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

Figure 1:
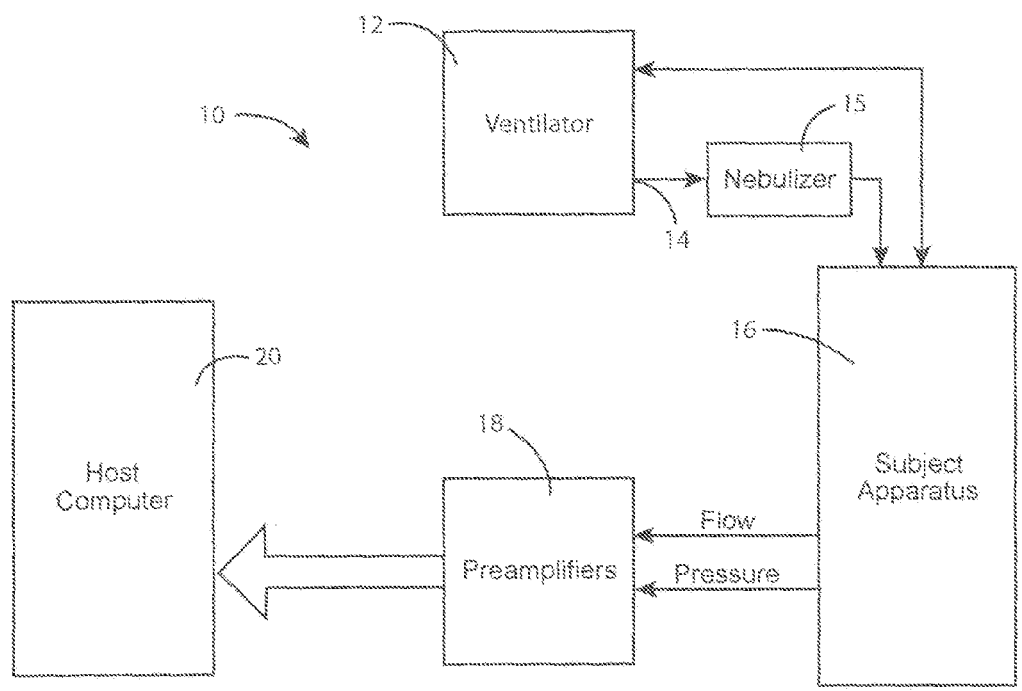
FIG. 1 is an illustration of the typical system components of a prior art ventilator.

FIG. 1 shows the basic components of a system, generally 10, commonly used for respiratory studies. The system includes a ventilator 12, nebulizer 15 placed inline between the inspiration port 14 and subject apparatus 16 enclosing the test subject, and preamplifier 18 to condition the flow and pressure signals from enclosure 16 so that host computer 20, typically a PC, can read the signals and analyze the results.

Ventilator 12 generally has 3 ports: inspiration port 22, expiration port 24, and exhaust port 26. Inspiration port 22 fills the lung. Expiration port 24 vents the lung. Exhaust port 26 may often be left open to atmosphere, but permits the researcher to either capture the expired gases, or maintain a minimum positive pressure on the lung (called positive end-expiratory pressure, or PEEP).

Figure 2:
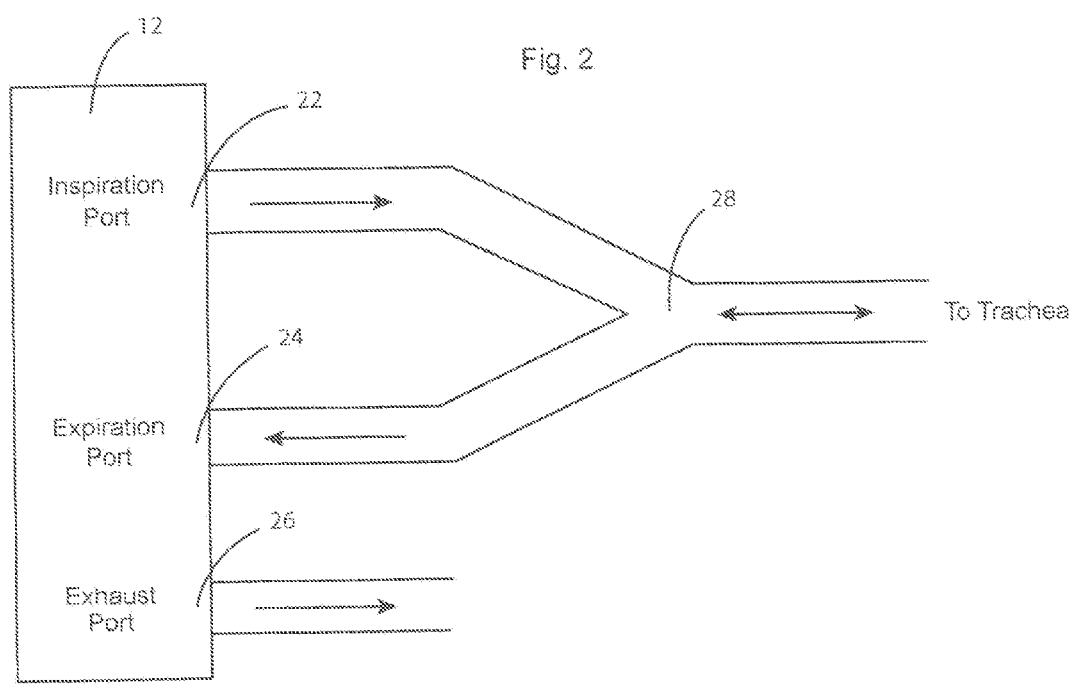
FIG. 2 is an illustration of the ventilator ports.

FIG. 2 shows how ports 22, 24 and 26 are connected to subject apparatus 16. Inspiration port 22 and expiration port 24 are connected with tubing 28 Y-junction which joins the two ports very near the trachea of the subject. The trachea is connected to the third port on the Y connector, with as little tubing as possible. This configuration minimizes the volume of air that the subject must take into its lungs before it gets fresh air from the ventilator, and therefore enables the animal to get maximum fresh air with each breath. Exhaust port 26 remains open to atmosphere. Another common configuration would call for tubing to be connected to exhaust port 26, with the free end of the tubing submerged a couple centimeters below the surface of a water column.

Figure 3:
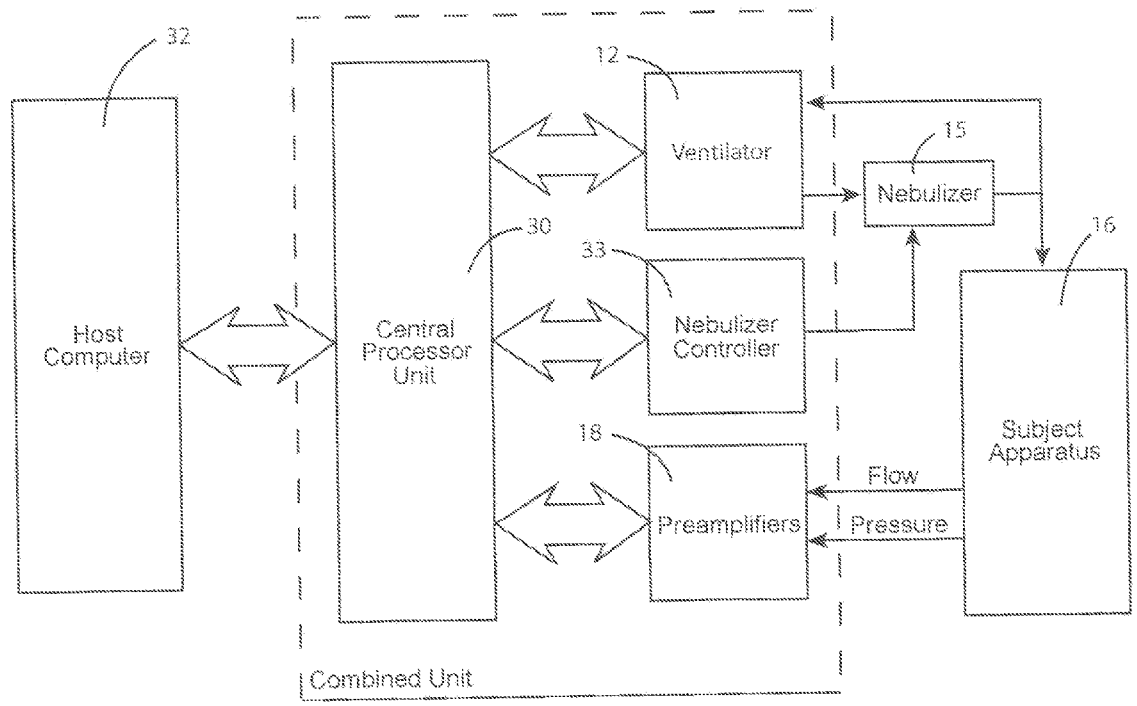
FIG. 3 is a diagram of the integrated ventilator.

The components of ventilator 12 are preferably combined into a single unit as shown in FIG. 3. With the aid of dedicated central processor unit 30, a new level of system intelligence is achieved because these previously separate tools can be coordinated to operate as one in order to achieve specific goals. Within this unit, processor 30 coordinates a set of specific actions as directed by host computer 32. Processor 30 controls the breathing of the subject using information relating to 1) target breathing rate, 2) maximum inspiration volume, and 3) maximum mouth pressure. In addition, it is the goal of ventilator 12 to shape the inspiratory flow pattern in order to deliver the air in a way which is more comfortable to the subject. The expiratory flow pattern is passive. That is, ventilator 12 does not attempt to actively control the flow of air out of the lungs beyond simply permitting the air to flow.

Figure 4:
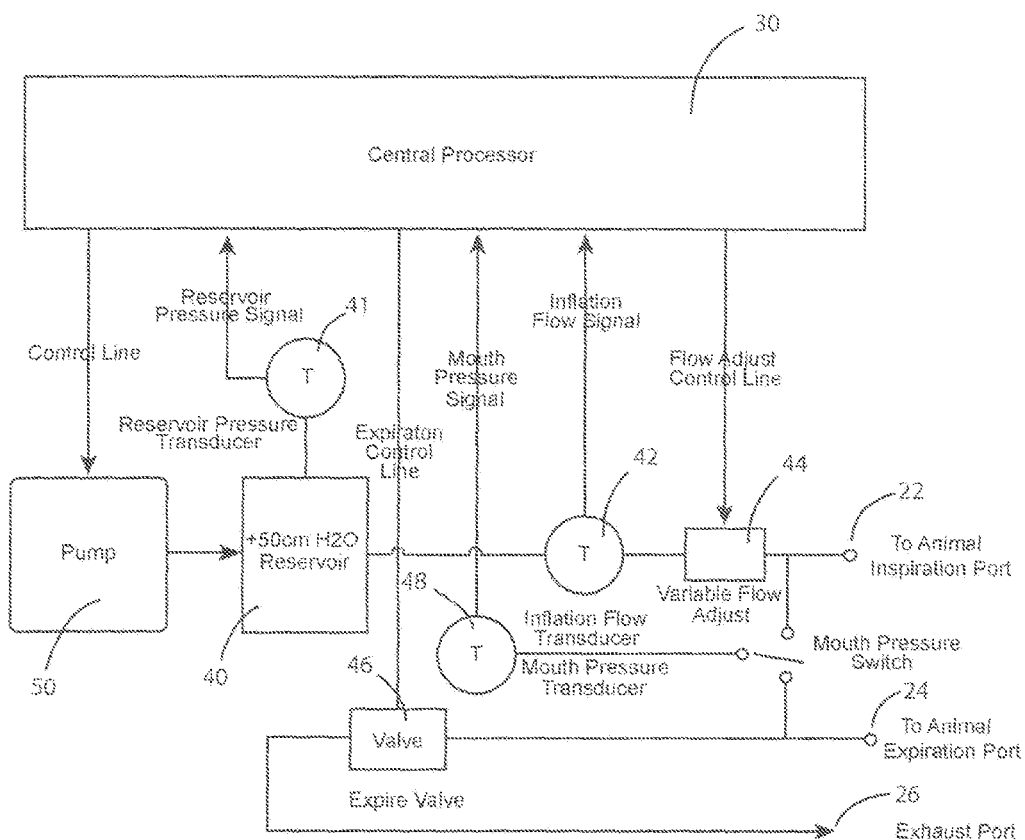
FIG. 4 is a detailed diagram of the components that the processor uses to ventilate the subject.

FIG. 4 details the components that processor 30 uses to ventilate the subject. As shown in the diagram, respirator ports 22, 24 and 26 are shown on the right. The air which is delivered into the subject's lungs is regulated to a safe pressure in reservoir 40. The reservoir pressure signal is conveyed to processor 30 from reservoir 40 via reservoir pressure transducer 41. The air flow from reservoir 40 through flow transducer 42 and flow adjust 44 before it is made available to the subject. Flow transducer 42 provides the processor with the air flow into the lung at any time. Flow adjust 44 permits the processor to control the air flow by adjusting the air resistance between reservoir 40 and the inspiration port 22.

Exhaust valve 46 opens during expiration to permit the air to flow out from the lung to the exhaust port. During this time, flow adjust valve 44 is closed (infinite resistance). During inspiration, exhaust valve 46 is closed.

Mouth pressure is measured at either the inspiration port 22 or the expiration port 24, depending upon where ventilator 10 is in the breath cycle. During inspiration, when expiratory valve 46 is closed, mouth pressure transducer 48 measures the pressure at expiration port 24. During expiration, the mouth pressure is measured at inspiration port 22. In other words, mouth pressure transducer 48 measures pressure in static non-moving air in order to get accurate pressure measurements.

Pressure reservoir 40 is designed to either operate with normal air, or with an optional external tank in the event the user wants to ventilate the subject with some special gases. One example of the former case would be if the user wants to incorporate inhaled anesthesia into the ventilation mixture.

Figure 5:
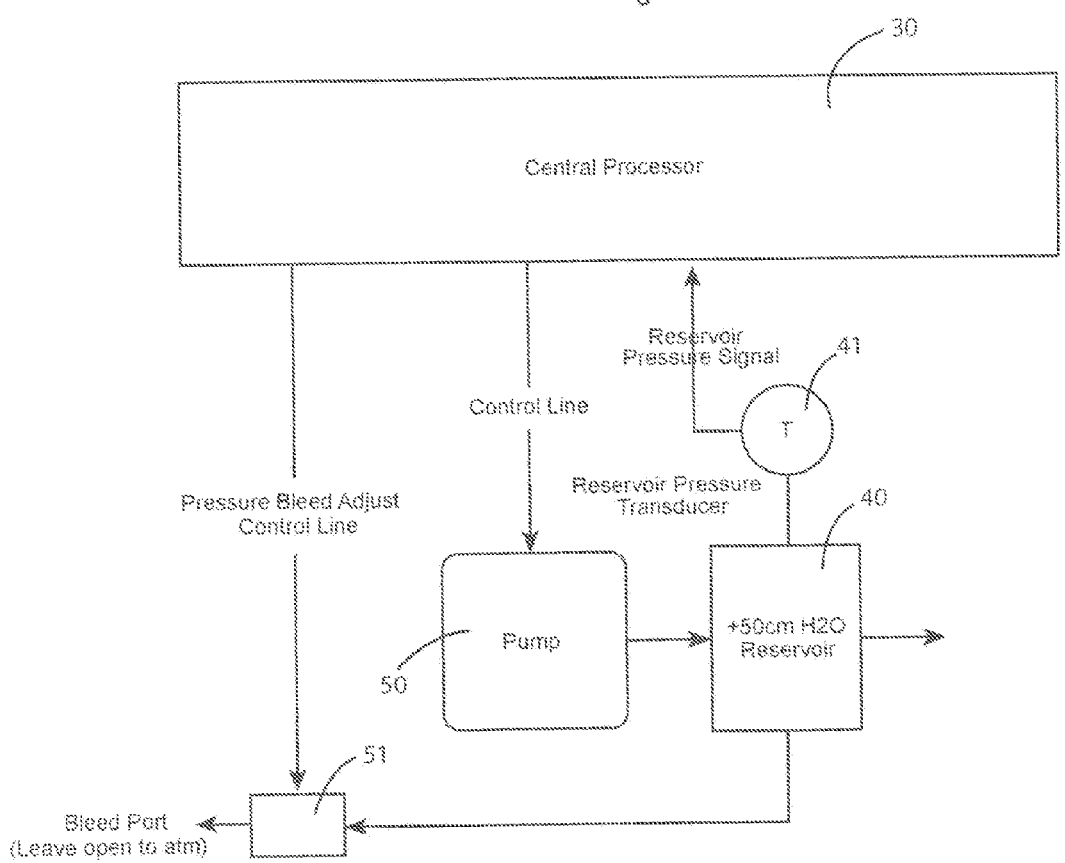
FIG. 5 is a configuration of the reservoir when the subject is ventilated with normal air.

FIG. 5 shows the configuration that is used when the subject is ventilated with normal air. This diagram shows the components used to regulate the pressure in the reservoir, and the flow of air into and out of the reservoir, when ventilating the subject with normal air. In this configuration, the system senses that the pressure is too low, so it turns on pump 50, and controls the variable bleed adjust 51 for precise pressure control. Pump 50 cannot respond too quickly so variable bleed adjust 51 is necessary to control the bleed off of excess pressure in the reservoir.

Figure 6:
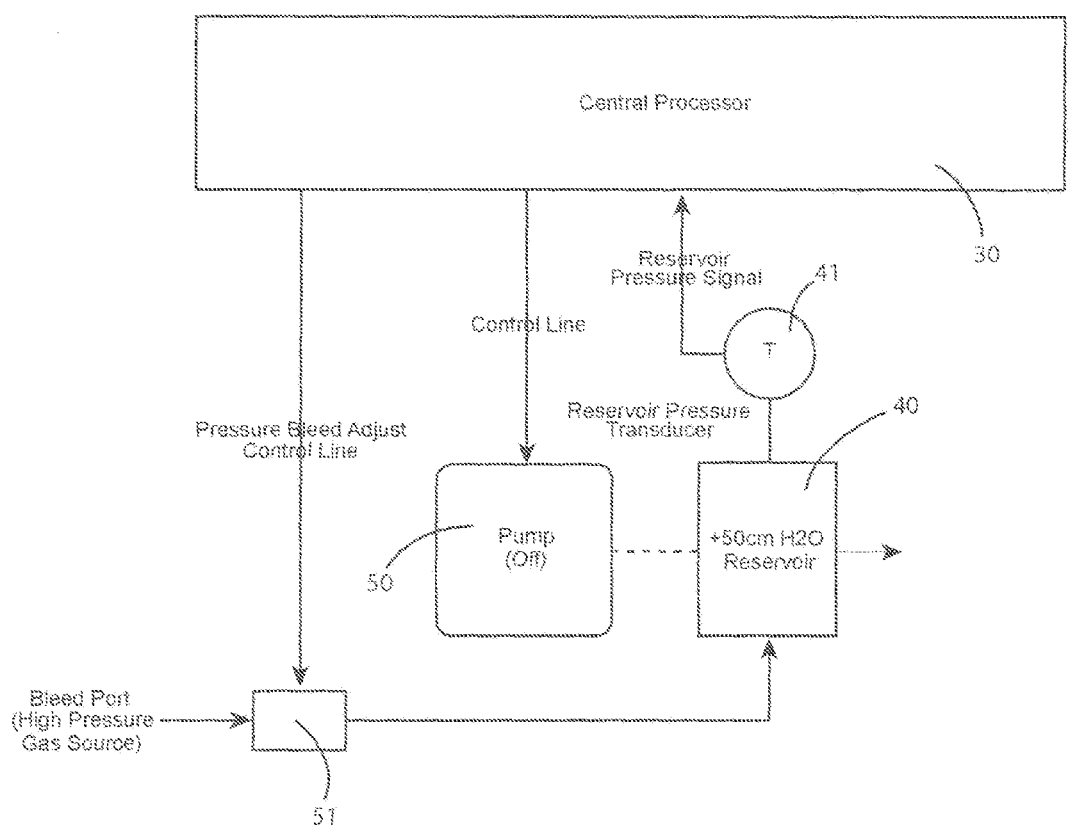
FIG. 6 is a configuration of the reservoir when the subject is ventilated with a gas source.

FIG. 6 illustrates the configuration when the subject is ventilated with a gas source. This diagram shows the pressure regulator and the flow of air into and out of reservoir 40 when a pressurized gas tank feeds reservoir 40. In this configuration, pump 50 is turned off. A pressurized tank of the ventilation mixture is connected to the bleed port. Processor 30 controls the variable bleed adjust 51 to permit more air through the bleed port.

Processor Controlled Calibration

In the present invention calibration apparatus, generally 60, connected to ventilator 12, with processor 30 undertaking automated steps to precisely calibrate the following five signals: 1) flow, 2) lung pressure, 3) inspiration flow, 4) mouth pressure, and 5) reservoir pressure.

Figure 7:
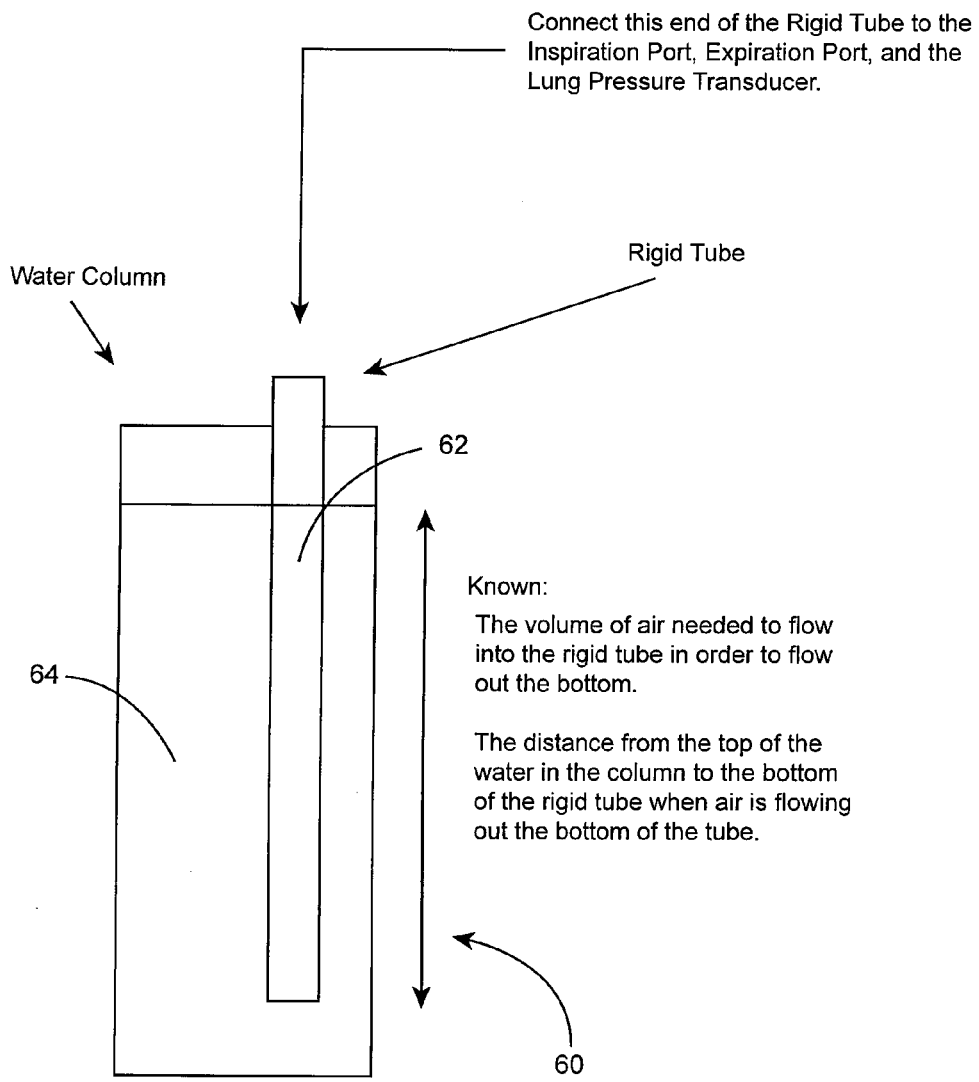
FIG. 7 illustrates the calibration apparatus used by the system to provide known pressure and flow levels.

FIG. 7 illustrates the calibration apparatus 60 used by this system to provide known pressure and flow levels. Calibration apparatus 60 allows the system to apply two known pressure levels, and to measure two known flows.

Figure 8:
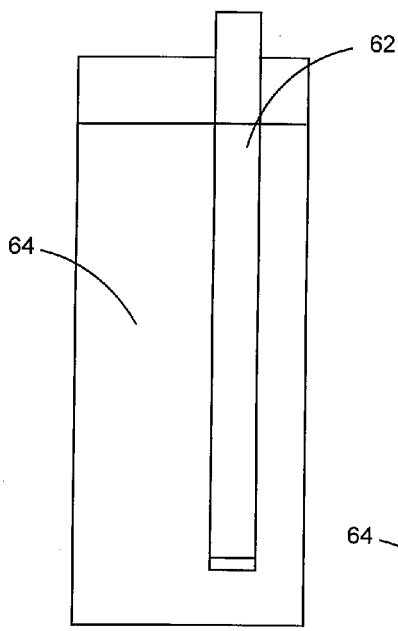
FIG. 8 illustrates the calibration apparatus when no air is flowing through it.

FIG. 8 shows calibration apparatus 60 when no air is flowing through it. When no air flows through it, the water level in rigid tube 62 is the same as the water level in the water column 64. Also, no air is bubbling up from the bottom of rigid tube 62. In this configuration, the pressure inside the tube is 0 cm $H_2O$.

Figure 9:
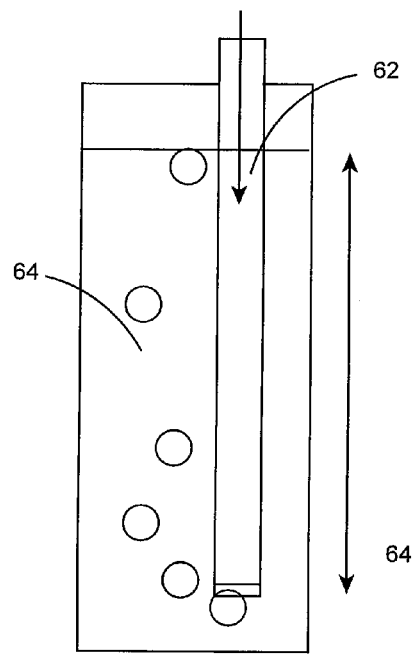
FIG. 9 illustrates the calibration apparatus with air flowing through it.

When air is allowed to flow into tube 62, and bubbling up from the bottom as shown in FIG. 9, then stopped, the pressure in tube 62 is the distance from the water level in column 64 to the bottom of rigid tube 62. FIG. 9 shows calibration apparatus 60 with air flowing through it. The air flowing into tube 62 is stopped, and then the air is allowed to flow out of tube 62, then a known amount of air will be forced by water column 64 out the top of tube 62. This known volume of air will be forced out within a limited and known amount of time. And since we know the volume in tube 62, and we know the time that it takes, then we know the average flow rate that the air moved in that time. That average flow rate is the second known flow for calibration.

Figure 10:
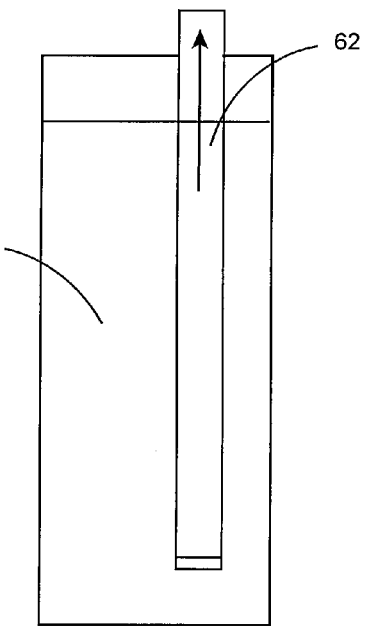
FIG. 10 shows the calibration apparatus when the pressure which was created when air was forced into tube 62 is about to be released.
Figure 11:
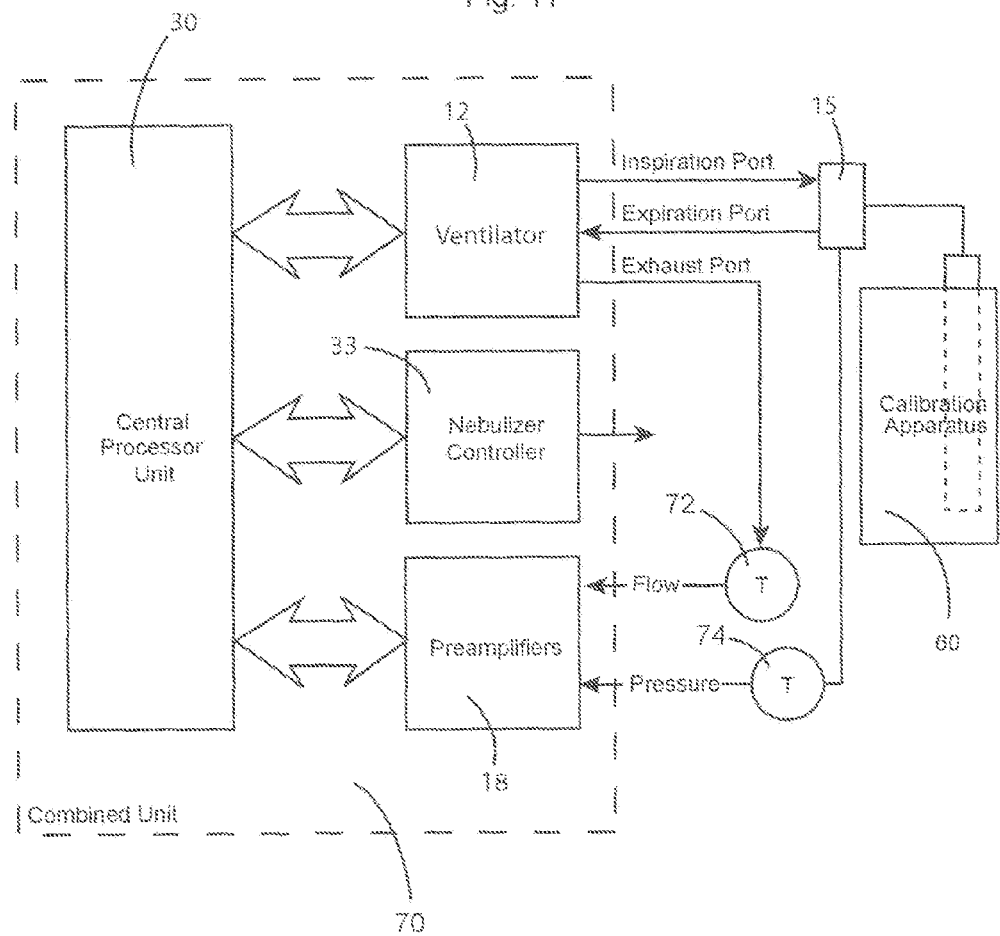
FIG. 11 illustrates the connection of the calibration apparatus to combined unit.
Figure 12:
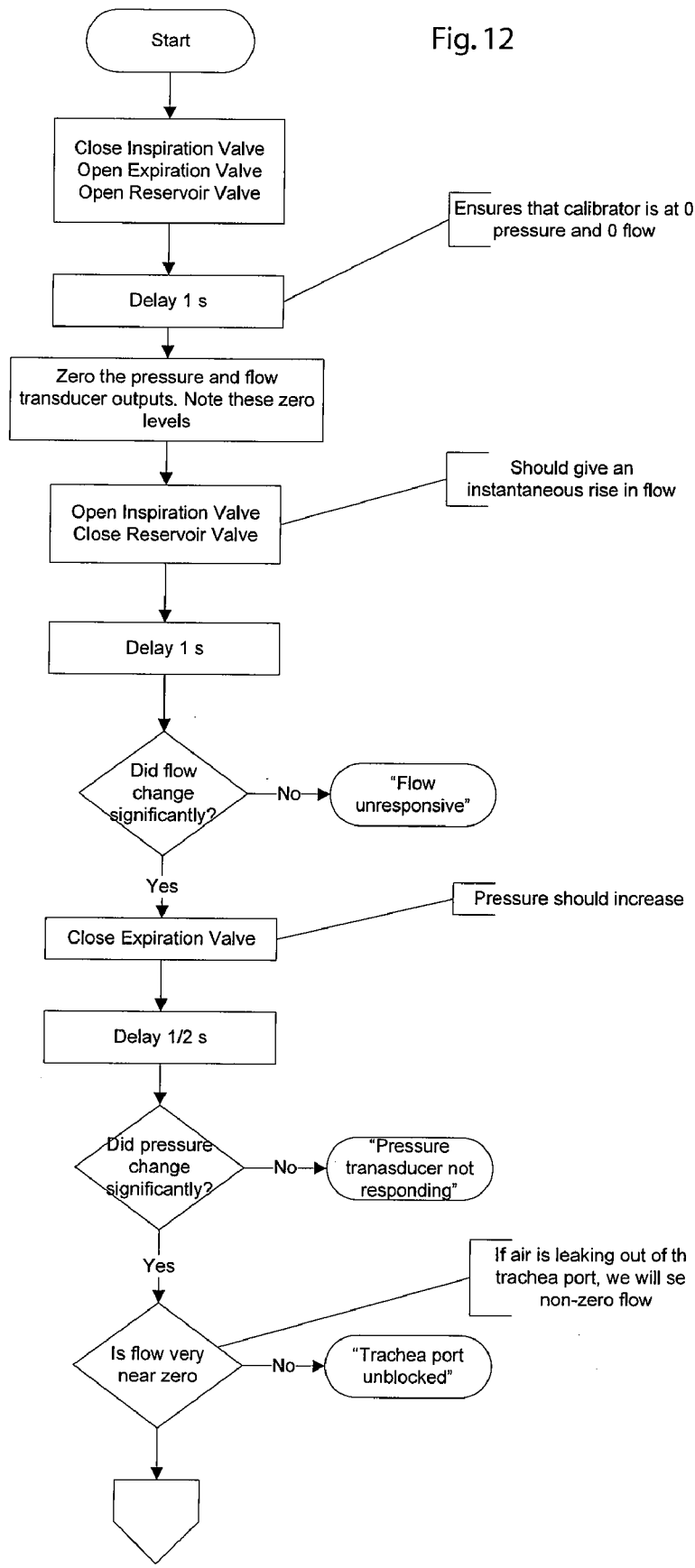
FIGS. 12-16 illustrate the routines and subroutines undertaken by the processor in calibrating the ventilator with the calibrator.
Figure 13:
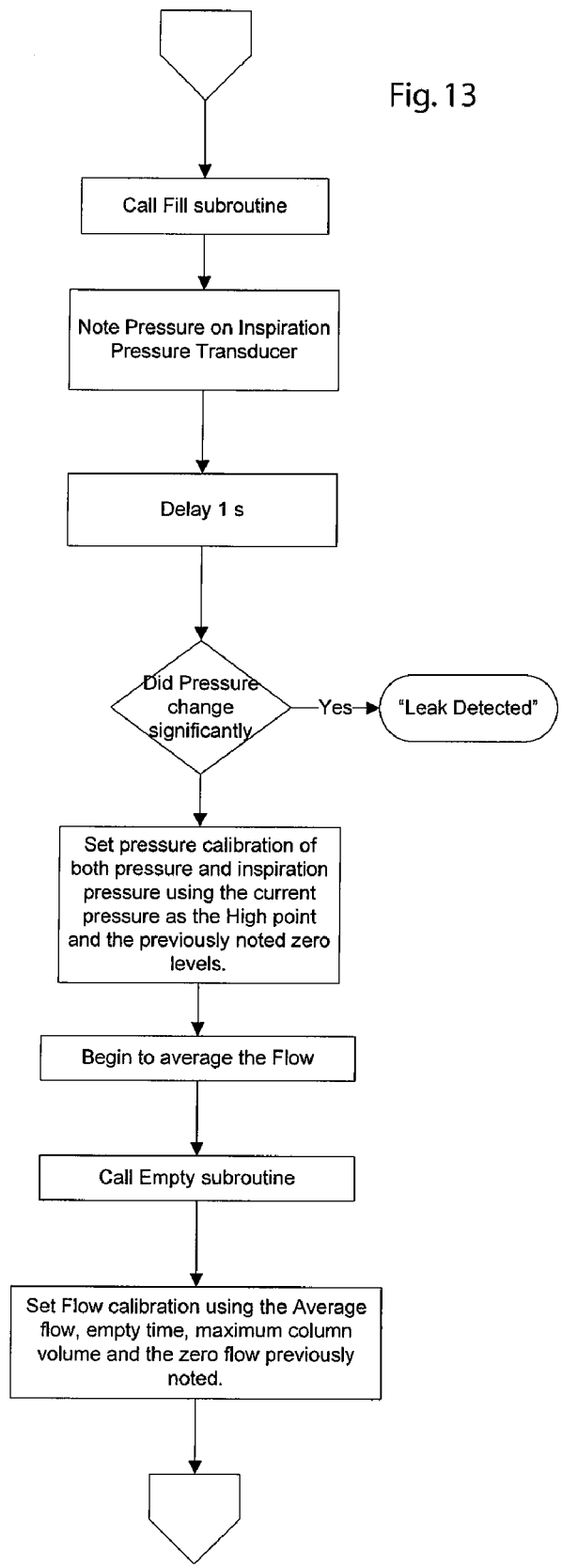
Figure 14:
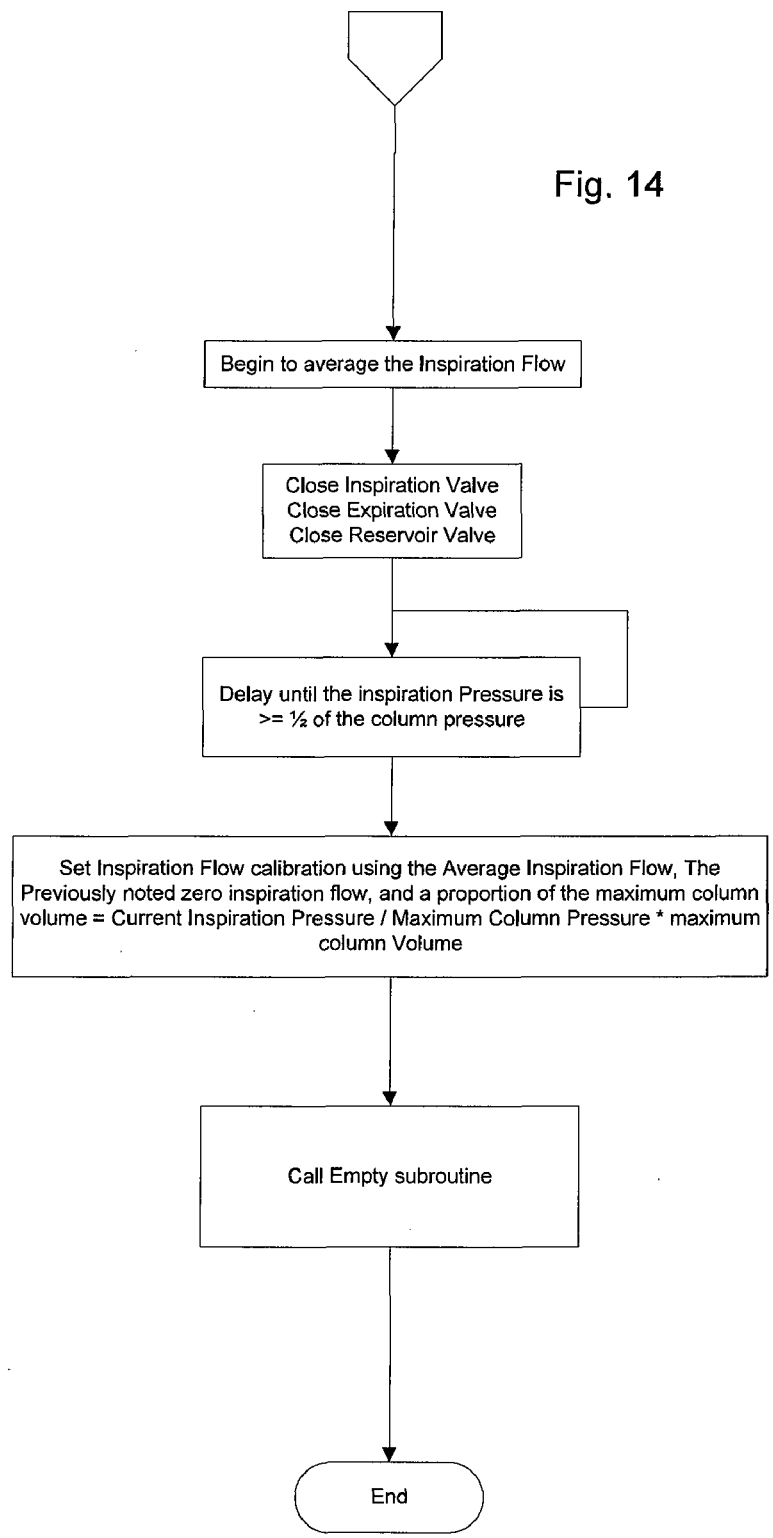
Figure 15:
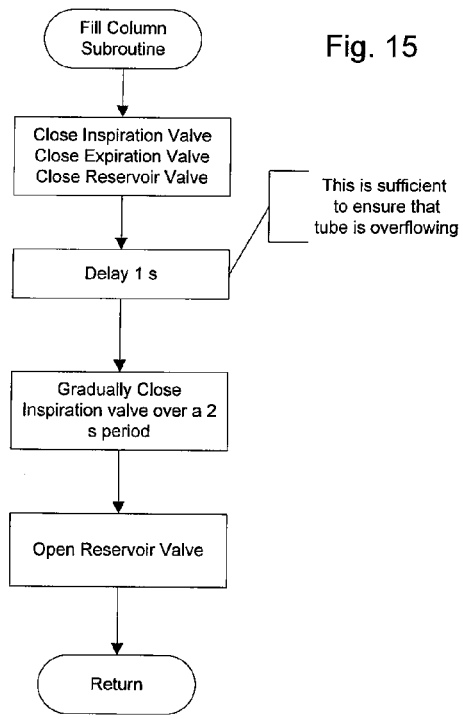
Figure 16:
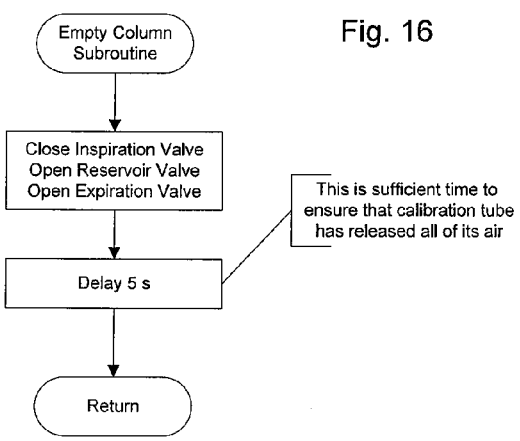

FIG. 10 shows the calibration apparatus 60 when the pressure which was created when air was forced into tube 62 is about to be released. To prepare for calibration, this apparatus should be connected to combined unit 70 and the flow transducer 72 and lung pressure transducer 74 in the following configuration. FIG. 11 illustrates how the user should connect calibration apparatus 60 to combined unit 70. As shown, nebulizer 15 does not need to be connected to nebulizer controller 33. Inspiration port 22, expiration port 24, calibration apparatus 60 and the lung pressure transducer 74 should all be connected together using tubing. The exhaust port 26 should be connected to external airflow transduce 72. The flow through the exhaust will provide a calibration flow which the system uses as a known flow.

Calibration of Lung Pressure, Mouth Pressure, and Reservoir Pressure

It is assumed that relationship between the signals from the pressure transducers and pressure is a straight line relationship. Therefore, the pressure transducers require only two known pressure calibration levels to establish the calibration. Processor 30 applies 0 cm $H_2O$ pressure to all the transducers. This is done by fully opening the inspiration valve, and simultaneously fully opening the reservoir bleed port.

Processor 30 applies a known pressure level as provided by calibration apparatus 60 by flowing air through inspiration port 22 and closing expiration port 24, and waiting until the air bubbles out the bottom of the rigid tube in calibration apparatus 60. At this time, the reservoir bleed port is adjusted until no bubbles flow out of the bottom of rigid tube 62. The pressure reading should be measured when the flow through rigid tube 62 is stopped, but the air still fills rigid tube 62.

The lung pressure, mouth pressure and reservoir pressure transducers are then calibrated by reading the transducer signals at each of these known levels and assuming a straight line relationship between the signal level and pressure.

Calibration of Subject Air Flow

Like the pressure transducers, air flow transducer 72 requires two known calibration flows to establish the calibration. Processor 30 applies 0 ml/sec flow through air flow transducer 72 by closing expiration port 24. This causes any air flowing through the exhaust port 26 to cease.

Processor 30 applies a second known flow through the air flow transducer 72 by performing the following:
1) Close the expiration port 24,
2) Turn on Inspiration flow 22 until air bubbles out the bottom of rigid tube 62 in calibration apparatus 60,
3) Shut off the inspiration flow,
4) Open expiration port.

Step 4 releases the air in rigid tube 62 and allows it to be forced out expiration port 24 and in turn out the exhaust port 26 and through air flow transducer 72. While that flow is not constant, we do know the volume, and we know the maximum time it takes to force that volume through. So by calculating the average flow over a region of time, we have a known flow we can use to calibrate.

The subject air transducer is then calibrated by reading the transducer signals at each of these known levels and assuming a straight line relationship between the signal level and subject air flow.

Calibration of Inspiration Flow

Calibration of inspiration flow, i.e., the inspiration flow transducer, is similar to calibration of subject air flow. However, this must be calibrated after the mouth pressure has been calibrated. Processor 30 applies 0 ml/sec through inspiration flow transducer 72 by closing inspiration port 22. The Processor 30 fills the inner column to some level. The processor can measure the level by measuring the pressure on the Mouth Pressure 48. Knowing the pressure, we know the level inside the inner column. Since the inner column is uniformly bored, the level inside the inner column is proportional to the volume of air in the inner column. So the volume filled can be calculated directly by measuring the mouth pressure. The known volume has been filled, so the average flow is then known by dividing that known volume by the time it takes to fill that volume.

Deep Breath Cycles

When assessing lung function, researchers commonly challenge the subject with a drug which causes the lungs to contract. They may challenge the subject several times at increasing doses of the drug in order to see how the reaction changes. Between each challenge, it is often necessary to open the lungs by forcing a few deep breaths. With current systems, researchers perform these deep breaths by covering the exhaust port 26 for about 3 breaths.

By covering exhaust port 26, the researcher prevents the subject from exhaling, and so, the subject takes a breath with 3 times as much volume as one breath. Processor 30 controls the deep breath in the same way that it controls a regular breath, except that the maximum volume and maximum pressure conditions are increased, and the desired breathing rate is disregarded.

Nebulizer Breath Cycles

While nebulizer 15 is producing aerosol, the ventilator can force the subject to breathe more deeply in order to deliver the aerosol more deeply into the lung. In addition, nebulizer 15 can be triggered to produce aerosol synchronous with the ventilator to most efficiently deliver the material to the lungs.

Electronically Controlled PEEP

Because the mouth pressure measurement switches to measure pressure at inspiration port 22 during expiration, this respirator can maintain PEEP without the use of a water column on the exhaust port 26 (which is typically done).

Integrated Blood Pressure or ECG Preamplifier

This system incorporates an integrated Blood Pressure or ECG preamplifier to monitor the life status of the subject.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:
1. A respiratory ventilator system comprising:
a) ventilator including inspiration and expiration ports, a pressurized air source, a pressure transducer for measuring it pressure, a flow transducer for measuring air flow, a flow control valve for regulating air flow, and a pressure regulator for regulating air pressure;
b) a processor for receiving air pressure and flow information from said transducers and controlling said flow control valve and air pressure in accordance with programmed instructions; and
c) a calibrator attachable to said inspiration port to calibrate said pressure and flow transducers, said calibrator measuring pressure transducer signals at two known pressure levels and flow transducer signals at two known flows and transmitting the measurements to said processor.

2. The ventilator system of claim 1, wherein said calibrator is comprised of a water-filled outer column, in inner column extending into said outer column, and tubing connecting the upper end of said inner column to said inspiration port.

3. The ventilator system of claim 2, wherein the first flow signal is zero, and the second flow signal is determined based on the volume of the inner tube and the time required to empty water from the inner tube.

4. The ventilator system of claim 2, wherein the first pressure signal is zero and the second pressure signal is determined by the pressure required to fill the inner tube with water.

5. The ventilator system of claim 1, further including a preamplifier, said signals being sent to said processor through said preamplifier.

6. The ventilator system of claim 1, wherein one of said pressure transducer signals and one of said flow signals are zero.

7. The ventilator system of claim 1, wherein said ventilator includes an exhaust port, and said flow transducer measures air flow from said exhaust port.

8. The ventilator of claim 1, wherein said ventilator includes an air pressure reservoir with a bleed port controlled by said processor to regulate air pressure in said ventilator.

9. The ventilator system of claim 1, wherein said processor assumes a straight line relationship between pressure levels and pressure signals, and between flow levels and flow signals.

10. The ventilator system of claim 1, including pressure transducers to measure lung pressure, mouth pressure and reservoir pressure, said processor calibrating each of said transducers based on information received from said calibrator.

11. A respiratory ventilator system comprising:
   a) a ventilator including inspiration and expiration ports, a pressurized air source, a pressure transducer for measuring air pressure, a flow transducer for measuring air flow, a flow control valve for regulating air flow, and a pressure regular for regulating air pressure;
   b) a processor for receiving air pressure and flow information from said transducers and controlling said flow control valve and air pressure in accordance with programmed instructions; and
   c) a calibrator attachable to said inspiration port to calibrate said pressure and flow transducers, said calibrator measuring pressure transducer signals at two known pressure levels and flow transducer signals at two known flows and transmitting the measurements to said processor, said calibrator including a water-filled outer column, a vertically aligned inner tube, and tubing connecting the inner tube to the inspiration port.

12. The ventilator system of claim 11, wherein said processor assumes a straight line relationship between pressure levels and pressure signals, and between flow levels and flow signals.

13. The ventilator system of claim 11, wherein the first flow signal is zero, and the second flow signal is determined based on the volume of the inner tube and the time required to empty water from the inner tube.

14. The ventilator system of claim 11, wherein the first pressure signal is zero and the second pressure signal is determined by the pressure required to fill the inner tube with water.

15. The ventilator system of claim 11, including pressure transducers to measure lung pressure, mouth pressure and reservoir pressure, said processor calibrating each of said transducers based an information received from said calibrator.

16. A method of calibrating transducers within a respiratory ventilation system including a ventilator having an air conduit, inspiration and expiration ports, pressure and flow transducers adapted to emit signals proportional to the levels of air pressure and air flow within said conduit, said ventilator being controlled by a processor comprising:
   a) providing a calibrator including a water-filled outer column, a vertically aligned inner tube, tubing connecting the inner tube to the inspiration port;
   b) measuring pressure transducer signals at two known pressure levels and flow transducer signals at two known flows and transmitting the measurements to said processor; and
   c) calibrating said pressure and flow transducer with said processor from said pressure and flow signals assuming that there is a straight line relationship between the two pressure signals and the two flow signals.

17. The method of claim 16, wherein one of said pressure levels is measured when the water levels in the outer column and the inner tube are the same and the second signal is measured when the inner tube is filled with pressurized air.

18. The method of claim 16, wherein the first flow signal is measured when there is no flow, and the second signal is determined by measuring the flow of air from the inner tube after the inner tube has been filled with air.

19. The method of claim 16, wherein said transducers are calibrated assuming a straight line relationship between pressure levels and pressure signals, and between flow levels and flow signals.

20. The method of claim 16, wherein said ventilator system includes pressure transducers to measure lung pressure, mouth pressure and reservoir pressure, said method including calibrating each of said transducers based on information received from said calibrator.

* * * * *